US006203519B1

(12) United States Patent
Fagerström et al.

(10) Patent No.: US 6,203,519 B1
(45) Date of Patent: Mar. 20, 2001

(54) INSUFFLATOR ASSEMBLY

(75) Inventors: Per-Olof Fagerström, Bjärred; Ola Nerbrink, Lund; Henri Hansson, Helsingborg; Marika Nilsson Eirefelt, Lund; Ingrid Erjefält, Södra Sandby, all of (SE)

(73) Assignee: Astra Akiebolag, Sodertalje (SE)

( * ) Notice: Subject to any disclaimer, the term of this patent is extended or adjusted under 35 U.S.C. 154(b) by 0 days.

(21) Appl. No.: 09/029,597

(22) PCT Filed: Jan. 13, 1998

(86) PCT No.: PCT/SE98/00037

§ 371 Date: Feb. 26, 1999

§ 102(e) Date: Feb. 26, 1999

(87) PCT Pub. No.: WO98/31414

PCT Pub. Date: Jul. 23, 1998

(30) Foreign Application Priority Data

Jan. 16, 1997 (SE) .................................................. 9700104

(51) Int. Cl.[7] .................................................. A61M 37/00
(52) U.S. Cl. .................................................. 604/26; 604/27
(58) Field of Search .................................. 604/26–27, 23, 604/24, 25; 128/748, 747

(56) References Cited

U.S. PATENT DOCUMENTS 2,722,935 11/1955 Thompson et al. .................. 128/266
4,464,169 * 8/1984 Semm .................................. 604/26
4,878,894 * 11/1989 Sutter et al. .......................... 604/24
5,061,239 * 10/1991 Shiels .................................. 604/26
5,246,419 * 9/1993 Absten .................................. 604/26
5,273,531 12/1993 Knoepfler .............................. 604/58
5,360,396 * 11/1994 Chan .................................... 604/26
5,514,087 * 5/1996 Jones .................................... 604/26
5,542,412 8/1996 Century .
5,554,112 * 9/1996 Walbrink et al. ...................... 604/27
5,599,297 * 2/1997 Chin et al. ............................ 604/26
5,800,381 * 9/1998 Ognier .................................. 604/26

* cited by examiner

*Primary Examiner*—Sharon Kennedy
*Assistant Examiner*—Kevin C. Sirmons
(74) *Attorney, Agent, or Firm*—Fish & Richardson PC

(57) ABSTRACT

An insufflator assembly, comprising: an insufflator comprising a delivery component (1) for delivering powder into an airway of an animal, a metering component (3) for providing a dose of powder (P) to the delivery component (1) and an inlet for receiving a stream of gas; and means for providing a stream of gas to the inlet of the insufflator so as to carry the dose of powder (P) into the airway of the animal, the means comprising a chamber (45) of a predetermined volume for containing gas at a predetermined pressure above atmospheric, a pressurized gas source (9) for providing gas of a predetermined pressure to the chamber (45), a first valve (47) for selectively connecting the chamber (45) to the pressurized gas source (9) and a second valve (49) for selectively connecting the chamber (45) to the inlet of the insufflator.

22 Claims, 6 Drawing Sheets

INSUFFLATOR ASSEMBLY

The present invention relates to an insufflator and an insufflator assembly incorporating the same.

Insufflator assemblies are known for blowing or forcing doses of powder containing medicament into the lungs of animals. In particular, insufflator assemblies are used during pharmaceutical trials to deliver powder containing medicament into the lungs of small animals, such as mice.

The dose of powder delivered to small animals is particularly small, typically in the range of from 20 to 25 $\mu$g. As such, it is difficult both to measure a dose of powder accurately and to provide a dose of powder in such a manner that the entire dose of powder is carried into the lungs of an animal.

In addition, the lungs of small animals are comparatively small, such that only a small volume of air can be used to deliver a dose of powder. Typically, for mice, the tidal volume, that is the volume of air passing into and out of the lungs in each breath, is only about 0.15 ml. As such, it is difficult to provide an air flow which will carry the entire dose of powder into the lungs of an animal without exceeding the capacity of the lungs of the animal.

One known insufflator assembly comprises a sample chamber connected between a delivery tube and a syringe. The sample chamber, which is of relatively large dimension, comprises two halves which are separated to load a dose of powder thereinto. In use, a dose of powder is loaded into the sample chamber and the delivery tube is then inserted into an airway of an animal, usually the laryngeal tract. The plunger of the syringe is then pushed rapidly into the body thereof so as to drive a predetermined volume of air through the sample chamber and carry the dose of powder from the sample chamber through the delivery tube and into the lungs of the animal.

In this known insufflator assembly the characteristics of the air flow are highly dependent upon how rapidly the user pushes the plunger of the syringe into the body thereof. In addition, the loading of powder into the sample chamber requires the user both to measure precisely a dose of powder and to ensure that the entire measured dose of powder is loaded into the sample chamber. Further, it is difficult to ensure that the entire dose of powder is delivered into the lungs of the animal.

Accordingly, the present invention provides an insufflator assembly, comprising: an insufflator comprising a delivery component for delivering powder into an airway of an animal, a metering component for providing a dose of powder to the delivery component and an inlet for receiving a stream of gas; and means for providing a stream of gas to the inlet of the insufflator so as to carry the dose of powder into the airway of the animal, the means comprising a chamber of a predetermined volume for containing gas at a predetermined pressure above atmospheric, a pressurized gas source for providing gas of a predetermined pressure to the chamber, a first valve for selectively connecting the chamber to the pressurized gas source and a second valve for selectively connecting the chamber to the inlet of the insufflator.

The present invention also provides a method of providing a stream of gas containing powder, comprising the steps of: pressurizing a chamber of a predetermined volume with gas at a predetermined pressure above atmospheric; sealing the chamber; and connecting the chamber to an inlet of an insufflator loaded with a dose of powder so as to release the pressurized gas into the insufflator and entrain the dose of powder in a stream of gas.

The present invention ensures that too great a volume of gas is not driven into the lungs of an animal. Indeed, the present invention can be configured to use an optimum volume of gas. Furthermore, since the insufflator assembly is triggered on the opening of only a single valve, the flow characteristics of the gas flow are substantially the same for each delivery. In particular, the flow characteristics are independent of the actions of a user.

The flow characteristics are particularly suited to powder delivery, since, on opening the second valve, gas of high pressure and high velocity is immediately released. In contrast, in known insufflator assemblies, there is a time lag while the pressure and the velocity of the gas flow builds up, such that the initial flow of gas is insufficient to carry powder and is hence wasted. The initial high pressure and high velocity gas flow achieved by the present invention is particularly effective in deagglomerating a packed dose of powder.

Preferably, the volume of gas delivered is from 1 to 2 ml.

The valves may be mechanical, but when the valves are any of pneumatic, electrical or magnetic, the insufflator assembly is more readily controllable. Preferably, at least the second valve should be a quick-opening valve.

In a preferred embodiment the second valve is connected to the insufflator by tubing of small bore and short length. In this way, a high pressure and high velocity gas flow is most effectively provided to the insufflator. This is because the dead space downstream of the chamber is minimized and there is only a small volume of gas in the tubing to be compressed, which compression will absorb part of the energy of the gas flow.

The present invention further provides an insufflator assembly, comprising: an insufflator for insertion into an airway of an animal and for delivering a dose of powder into the airway of the animal, the insufilator comprising a tube with two open ends; and a loading component comprising an elongate member having an end face for insertion into one end of the tube and for movement to a predetermined position proximate the other end of the tube so as to define a space between the other end of the tube and the end face of the elongate member, which space is in use filled with a dose of powder.

The present invention still further provides a method of loading a dose of powder into an insufflator comprising a tube with two open ends, comprising the steps of: inserting an elongate member of a loading component into one end of the tube, the elongate member having an end face; moving the end face of the elongate member through the tube to a predetermined position proximate the other end of the tube; and filling a space in the tube between the other end of the tube and the end face of the elongate member with a dose of powder.

In this way, a dose of powder is loaded directly into the tube from which it is delivered. Thus, additional steps of transferring a dose of powder intact to a delivery device are avoided. Furthermore, as the tube is of small dimension, the dose of powder may be accurately selected with relative ease by varying the volume of the space defined in the tube. In a preferred embodiment the volume of the space is set so as to provide a dose of powder of from 20 to 25 $\mu$g.

In a preferred embodiment the insufflator further comprises a further tube having two open ends, one end being for insertion into the airway of the animal and the other end being connectable with the other end of the first-mentioned tube.

The present invention yet further provides an insufflator for delivering a dose of powder into an airway of an animal, comprising: a first tube having two open ends, one end being for insertion into an airway of an animal; and a second tube having two open ends, one end for receiving a stream of gas and the other end being in use loaded with a dose of powder and connected to the other end of the first tube.

The present invention still yet further provides a method of providing a dose of powder in an insufflator for subsequent dispersion in a stream of gas, comprising the steps of: providing first and second connectable tubes; filling one end of one tube with a dose of powder; and connecting the one end of the one tube to one end of the other tube.

In this way, a dose of powder is provided directly in the flow path through the insufflator. In particular, the dose of powder is located at the inlet of the first tube such that the dose of powder can be delivered effectively therethrough.

Preferably, the other end of the second tube is inserted into the other end of the first tube.

The present invention contemplates for the first time that the airways with which the insufflator may be used include nasal passageways and that powder containing medicament may be delivered to the nasal cavities. Thus, the present invention extends to a method of delivering powder containing medicament to nasal cavities by inserting an insufflator into a nasal passageway.

It will be appreciated that whilst the present invention is described in relation to use with animals the present invention can equally be used with humans.

Medicaments suitable for administration by the present invention are any which may be delivered into airways and include for example β2-adrenoreceptor agonists, for example, salbutamol, terbutaline, rimiterol, fenoterol, reproterol, adrenaline, pirbuterol, isoprenaline, orciprenaline, bitolterol, salmeterol, formoterol, clenbuterol, procaterol, broxaterol, picumeterol, TA-2005, mabuterol and the like, and their pharmacologically acceptable esters and salts; anticholinergic bronchodilators, for example, ipratropiumn bromide and the like; glucocorticosteroids, for example, beclomethasone, fluticasone, budesonide, tipredane, dexamethasone, betamethasone, fluocinolone, triamcinolone acetonide, mometasone and the like, and their pharmacologically acceptable esters and salts; antiallergic medicaments, for example, sodium cromoglycate and nedocromil sodium; expectorants; mucolytics; antihistamines; cyclooxygenase inhibitors; leukotriene synthesis inhibitors; leukotriene antagonists; phospholipase-A2 (PLA2) inhibitors; platelet aggregating factor (PAF) antagonists and prophylactics of asthma; antiarrhythmic medicaments; tranquilisers; cardiac glycosides; hormones; antihypertensive medicaments; antidiabetic medicaments; antiparasitic medicaments; anticancer medicaments; sedatives; analgesic medicaments; antibiotics; antirheumatic medicaments; immunotherapies; antifungal medicaments; antihypotension medicaments; vaccines; antiviral medicaments; proteins; polypeptides and peptides, for example, peptide hormones and growth factors; polypeptide vaccines; enzymes; endorphines; lipoproteins and polypeptides involved in the blood coagulation cascade; vitamins; and others, for example, cell surface receptor blockers, antioxidants, free radical scavengers and organic salts of N,N'-diacetylcystine.

Preferred embodiments of the present invention will now be described hereinbelow by way of example only with reference to the accompanying drawings, in which.

Figure 1:
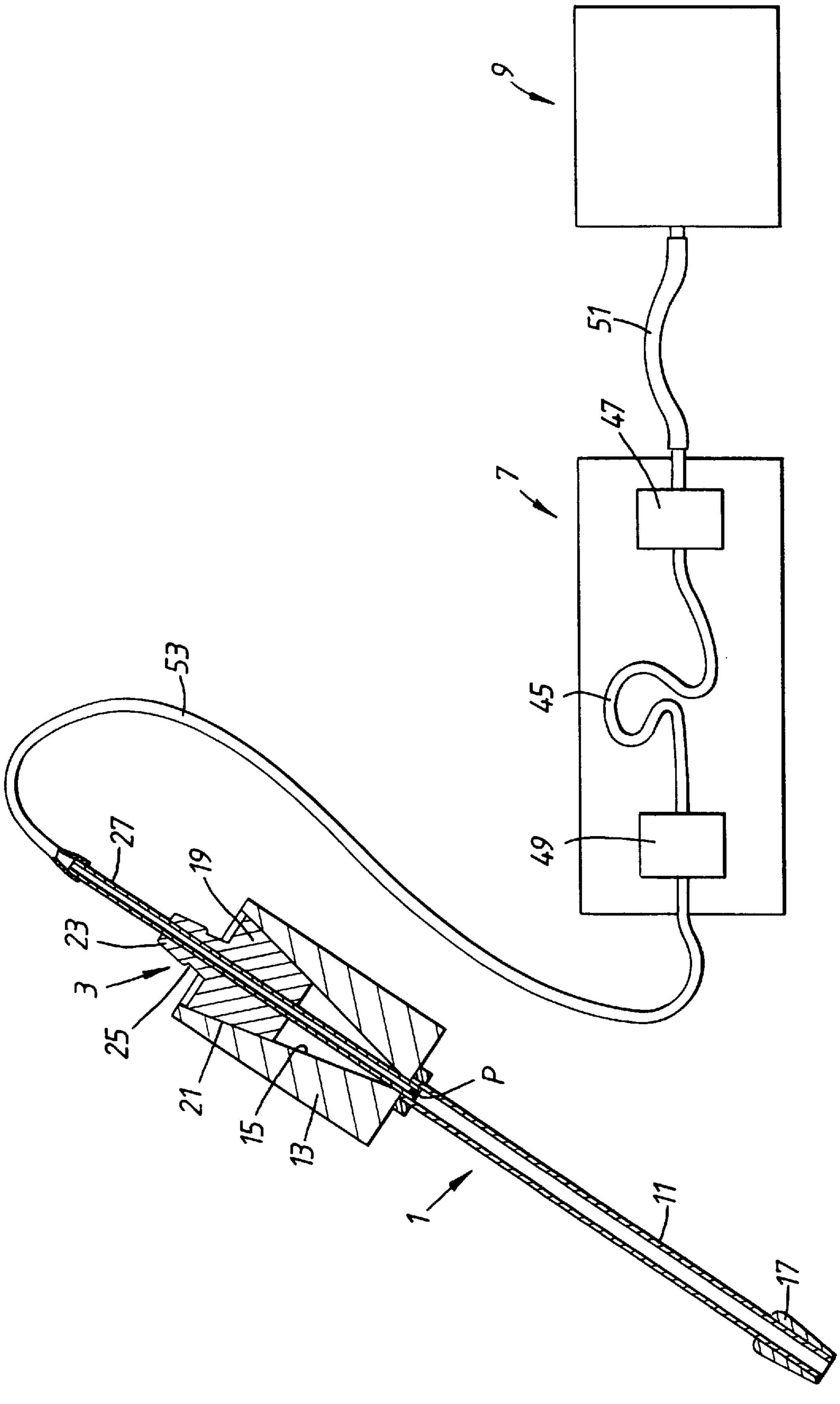
FIG. 1 illustrates the principal elements of an insufflator assembly in accordance with a first embodiment of the present invention.
Figure 2:
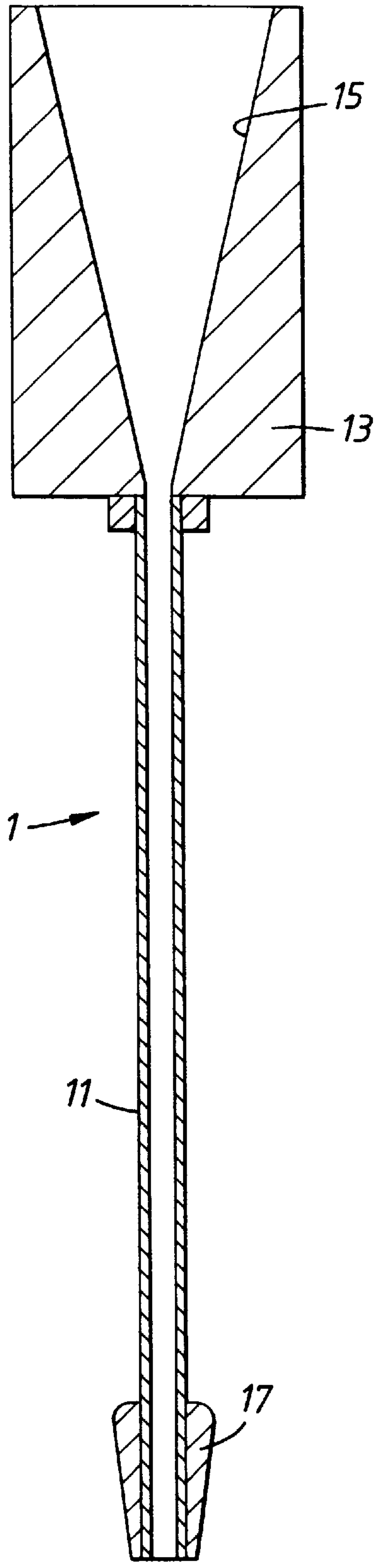
FIG. 2 illustrates the delivery component of the insufflator of the insufflator assembly of the first embodiment of the present invention.
Figure 3:
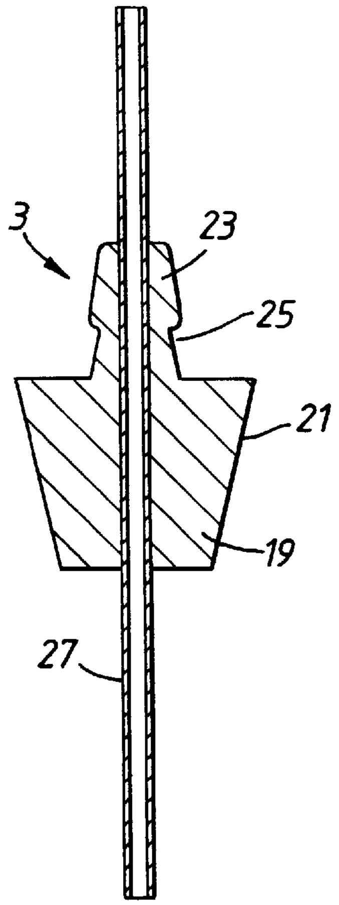
FIG. 3 illustrates the metering component of the insufflator of the insufflator assembly of the first embodiment of the present invention.

In a first embodiment the insufflator assembly comprises an insufflator comprising a delivery component 1 for delivering powder into the laryngeal tract of an animal and a metering component 3 for providing a dose of powder to the delivery component 1, a loading component 5 for use in loading a dose of powder into the metering component 3 of the insufflator and an air supply means comprising a firing unit 7 and a pressurized air source 9 connectable to the insufflator for providing an air flow to carry the dose of powder into the lungs of the animal.

The delivery component 1 comprises a delivery tube 11 for insertion into the laryngeal tract of an animal, which delivery tube 11 is preferably a cannula similar to the needle of a syringe and may be metallic. One end of the delivery tube 11 is provided with a connector 13 having an inwardly tapered frusto-conical portion 15 for receiving the metering component 3. The other end of the delivery tube 11, which is inserted into the laryngeal tract, is preferably provided with a conically, olived or droplet shaped portion 17 so as to minimise trauma to the laryngeal tract during insertion. Preferably, the connector 13 is a standard syringe connector, such as a Luer connector.

The metering component 3 comprises a connector 19 having a frusto-conical portion 21 which is adapted to fit into and seal with the frusto-conical portion 15 of the connector 13 of the delivery component 1. The connector 19 further has an extension 23 in which is formed a peripheral groove 25. The metering component 3 further comprises a metering tube 27 which extends through the connector 19. One end of the metering tube 27, in this embodiment that end extending from the small end on the connector 19, is shaped and dimensioned to locate within at least an end part of the delivery tube 11 of the delivery component 1.

In this embodiment, as illustrated in FIG. 1, the outer dimension of the metering tube 27 is substantially the same as the inner dimension of the delivery tube 11 such that the metering tube 27 and the delivery tube 11 are generally in sealing engagement when the metering component 3 is fitted to the delivery component 1 and the metering tube 27 is inserted into the delivery tube 11. In this way, a high pressure air flow is introduced directly into the delivery tube 11 and it is therefore unnecessary for the connection between the frusto-conical portions 15, 21 of the connectors 13, 19 to withstand such pressures. Accordingly, whereas traditional Luer locks use stainless steel connectors, the connectors 13, 19 can be formed from other materials, such as plastics materials.

Figure 4:
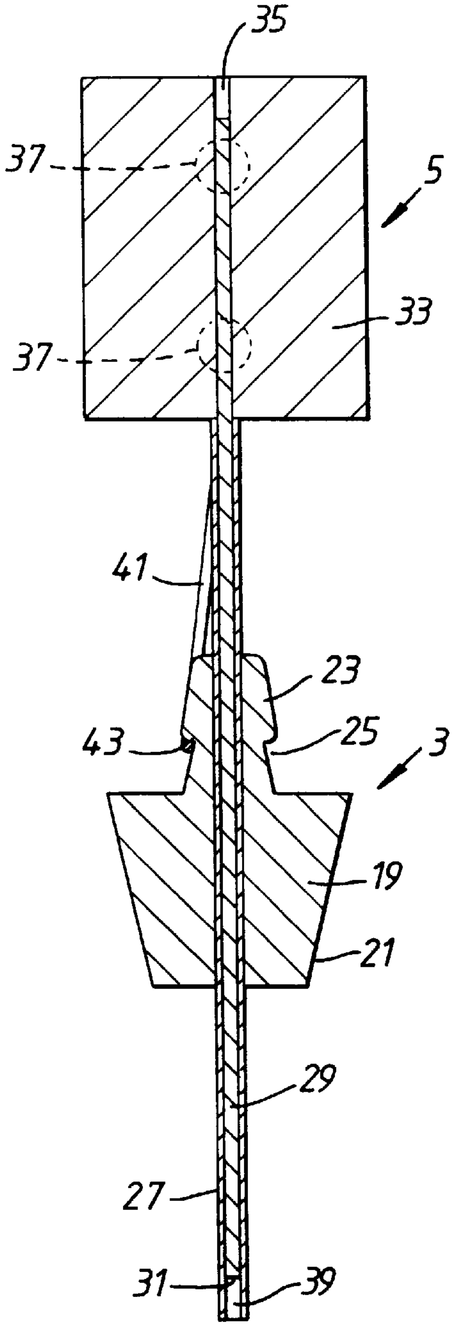
FIG. 4 illustrates the metering component of the insufflator and the loading component when fitted together of the insufflator assembly of the first embodiment of the present invention.
Figure 5:
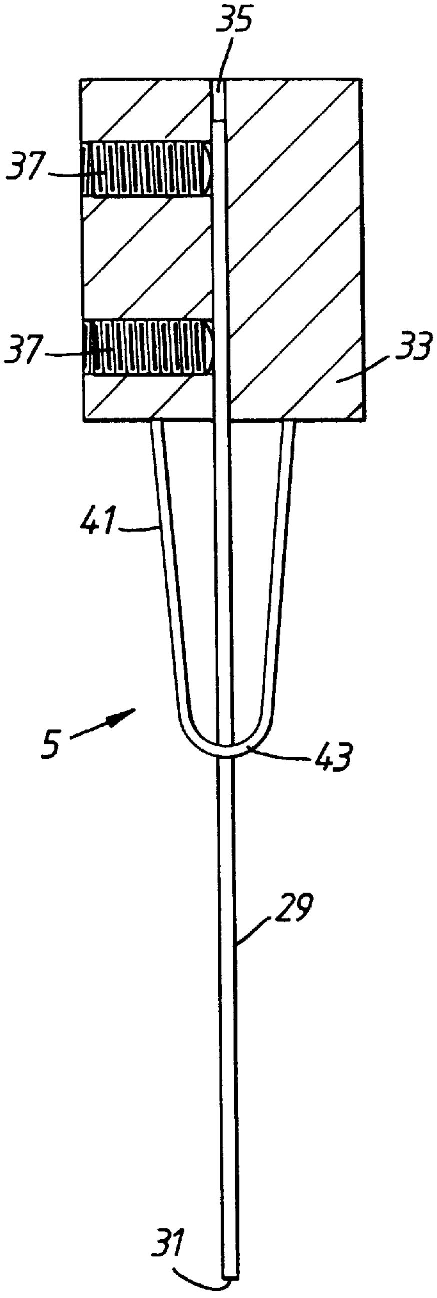
FIG. 5 illustrates the loading component of the insufflator assembly of the first embodiment of the present invention.

The loading component 5, which is used to load a dose of powder into the metering component 3, comprises an elongate member 29 having an end face 31 with an outer dimension substantially the same as the inner dimension of the metering tube 27 and a stop 33 adjustably mounted to one end of the elongate member 29. In this embodiment the stop 33 includes a through slot 35 in which the elongate member 29 is slidable, with the stop 33 being fixed in position relative to the elongate member 29 by screws 37 which are tightened against the elongate member 29. When the loading component 5 is fitted to the metering component 3, as illustrated in FIG. 4, the stop 33 restricts how far the elongate member 29 is inserted into the metering tube 27. The length of the elongate member 29 protruding beyond the stop 33 is selected such that a space 39 of predetermined volume is defined by the inner surface of the metering tube 27 and the end face 31 of the elongate member 29 at the distal end of the metering tube 27.

The loading component 5 further comprises a sprung component 41 which acts to retain the loading component 5 in a fixed position relative to the metering component 3 when fitted thereto. One end 43 of the sprung component 41, in this embodiment a U-shaped sprung member, is resiliently biased towards the elongate member 29. When the elongate member 29 is inserted into the metering tube 27, the end 43 of the sprung component 41 is located in the peripheral groove 25 in the extension 23 of the connector 19. In this way, the loading component 5 is securely retained relative to the metering component 3 during the step of filling the space 39 with a dose of powder.

As will be apparent, the end face 31 of the elongate member 29 should generally seal with the inner surface of the metering tube 27 at least in so far as is necessary to prevent any significant amount of powder passing beyond the end face 31. Preferably, for the purposes of providing a good seal and imparting linearity to the adjustment of the volume of the space 39 with movement of the elongate member 29, the end section of the inner surface of the metering tube 27 is of uniform cross-section. The length of this end section need only be as long as that of the required length of adjustment. Nevertheless, in a preferred embodiment, the entire length of the inner surface of the metering tube 27 is of uniform cross-section and the elongate member 29 comprises a rod having an outer surface with a cross-section substantially the same as that of the inner surface of the metering tube 27. In another embodiment the end face 31 of the elongate member 29 can be provided with a seal, such as a cup seal. However, whilst providing an excellent seal, this arrangement tends to make dosing accuracy more difficult to determine.

In use, with the loading component 5 fitted to the metering component 3, the space 39 is filled with a predetermined dose of powder P. Typically, the space 39 is filled by dipping the distal end of the metering tube 27 into powder so as to pack the space 39 with a dose of powder P. In practice, the distal end of the metering tube 27 is dipped more than once, preferably 20 to 30 times and more preferably 40 or more times, to ensure good packing. In a preferred embodiment the distal end of the metering tube 27 is actually pressed against a surface, preferably an elastic surface, such that powder is forced into the space 39. Ideally, powder would be provided in a small cap-like container with a rubber-like base or insert.

The metering component 3 may be fitted to the delivery component 1 before or after the loading component 5 is removed from the metering component 3. Owing to the nature of the very fine powder used, the dose of powder P will remain in a packed state within the metering tube 27 even if the loading component 5 is removed from the metering component 3 before fitting of the metering component 3 to the delivery component 1.

The firing unit 7 comprises a chamber 45, in this embodiment provided by a tube, of predeterminable volume having an inlet to which is provided a first valve 47 and an outlet which is provided a second valve 49. The use of a tube enables small volumes to be accurately determined and also ensures an air flow with good flow characteristics. The chamber 45 may be of fixed volume or may incorporate means for varying the volume according to particular requirements. In this embodiment the valves 47, 49 are magnetic valves, but any other easily controlled valves could be used. The inlet of the chamber 45 is connected via the first valve 47 to the pressurized air source 9 with tubing 51. The outlet of the chamber 45 is connected via the second valve 49 to the metering tube 27 of the metering component 3 of the insufflator with flexible tubing 53.

In use, with the second valve 49 closed and the first valve 47 open, the pressurized air source 9 fills the chamber 45 with air at a predetermined pressure. Once a stable condition has been reached, the first valve 47 is then closed. At this point, the firing unit 7 is ready for operation to drive the dose of powder P from the delivery tube 11. To drive the dose of powder P from the delivery tube 11, the second valve 49 is opened, thereby releasing the predetermined volume of pressurized air through the tubing 53, into the metering tube 27 where it entrains the dose of powder P and then out of the delivery tube 11.

Figure 6:
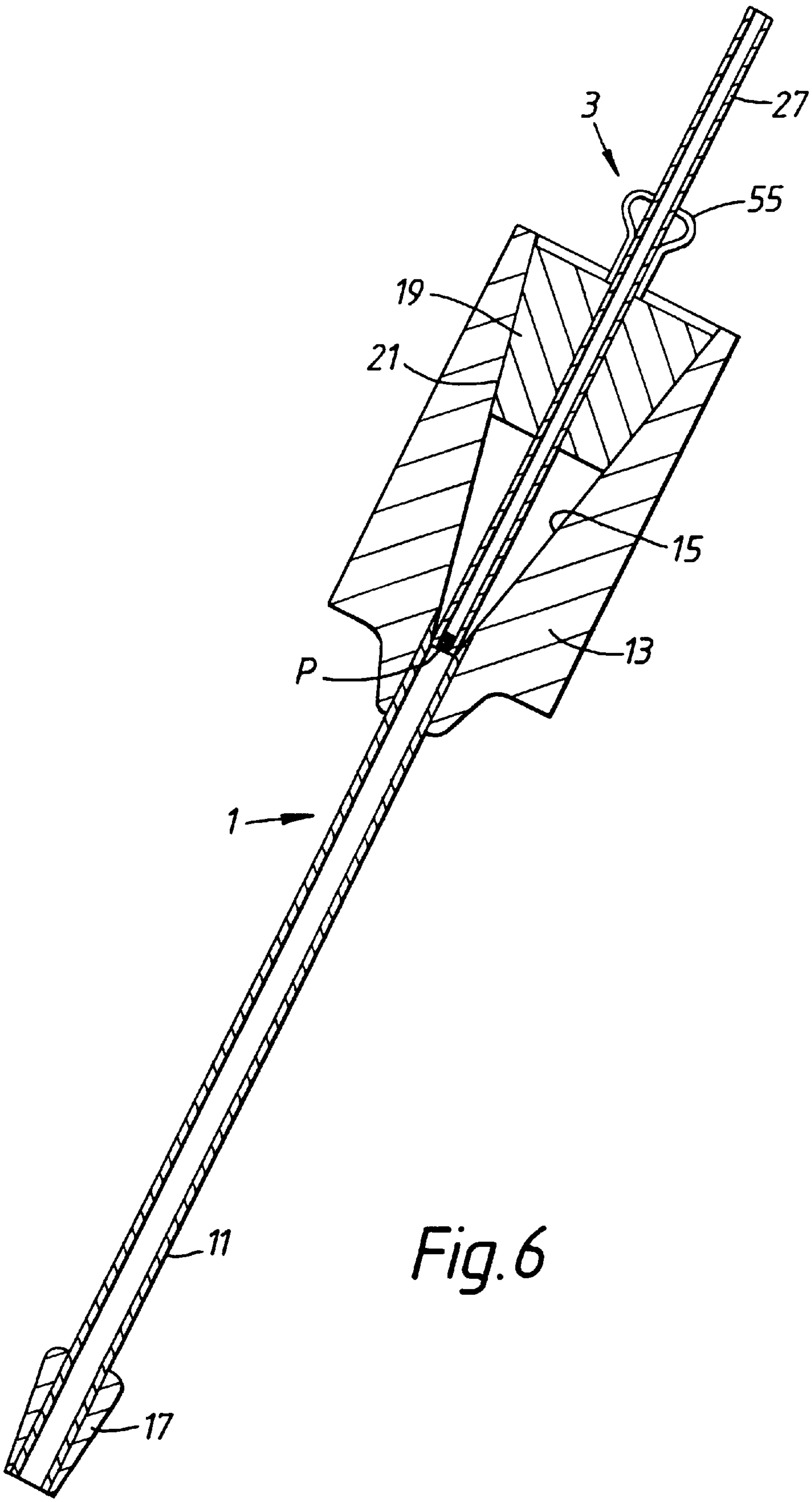
FIG. 6 illustrates the insufflator of an insufflator assembly in accordance with a second embodiment of the present invention.
Figure 7:
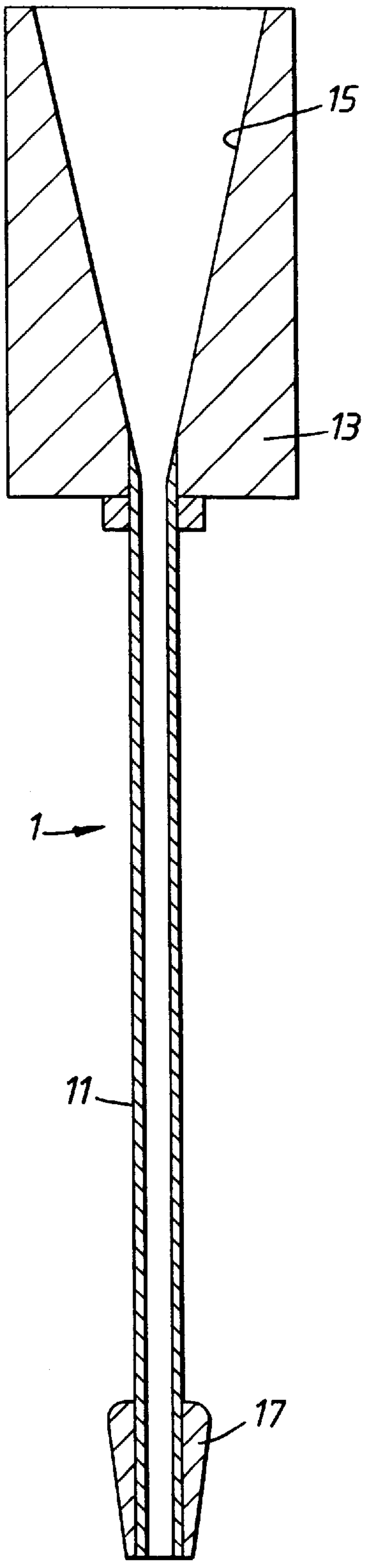
FIG. 7 illustrates the delivery component of the insufflator of the insufflator assembly of the second embodiment of the present invention.
Figure 8:
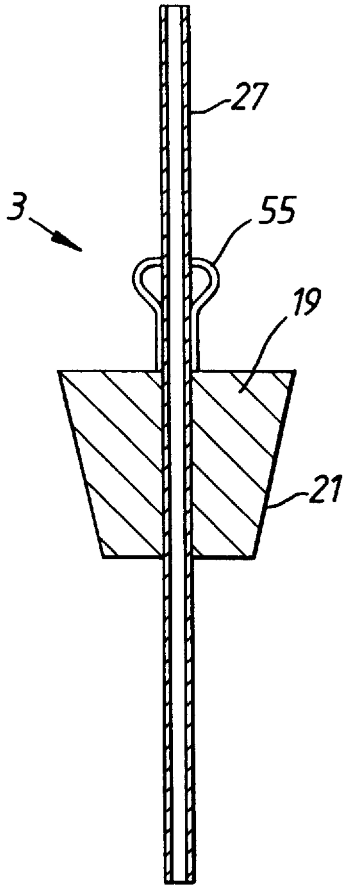
FIG. 8 illustrates the metering component of the insufflator of the insufflator assembly of the second embodiment of the present invention.

FIG. 6 illustrates the insufflator of an insufflator assembly in accordance with a second embodiment of the present invention. This insufflator is structurally quite similar to the insufflator of the above-described embodiment and in order not to unnecessarily duplicate description only the differences will be described. Operation of the insufflator is the same as that of the above-described embodiment.

In this embodiment the end of the delivery tube 11 of the delivery component 1 into which the metering tube 27 of the metering component 3 is fitted is tapered and the metering tube 27 has an outer dimension which is greater than the inner dimension of the delivery tube 11. In this way, the metering tube 27 abuts the tapering section of the delivery tube 11 when the metering component 3 is fitted to the delivery component 1.

Figure 9:
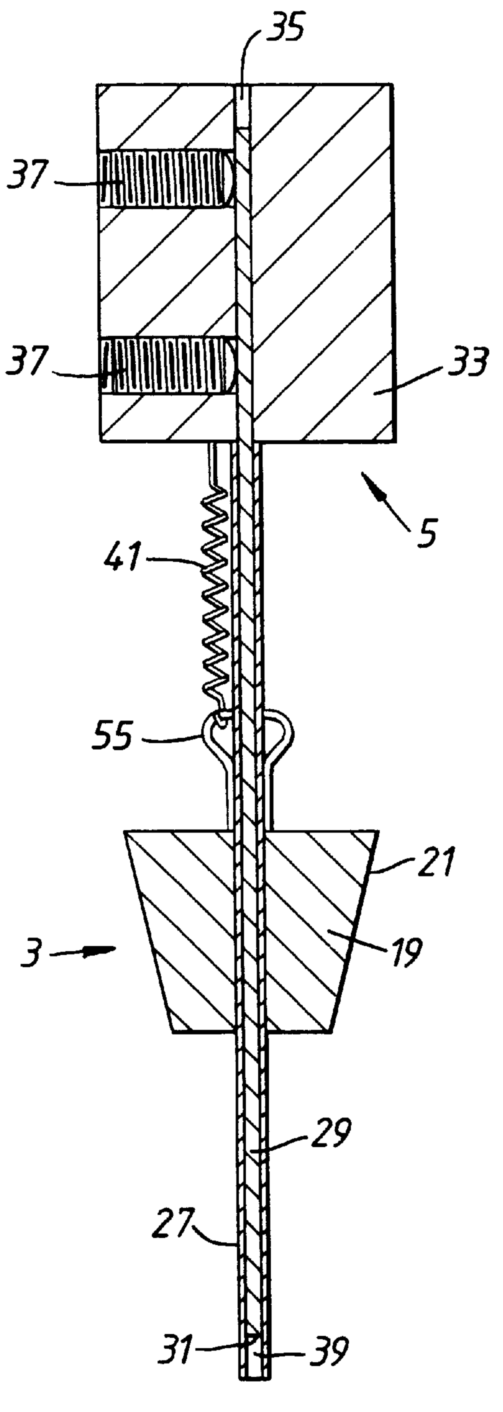
FIG. 9 illustrates the metering component of the insufflator and the loading component when fitted together of the insufflator assembly of the second embodiment of the present invention.
Figure 10:
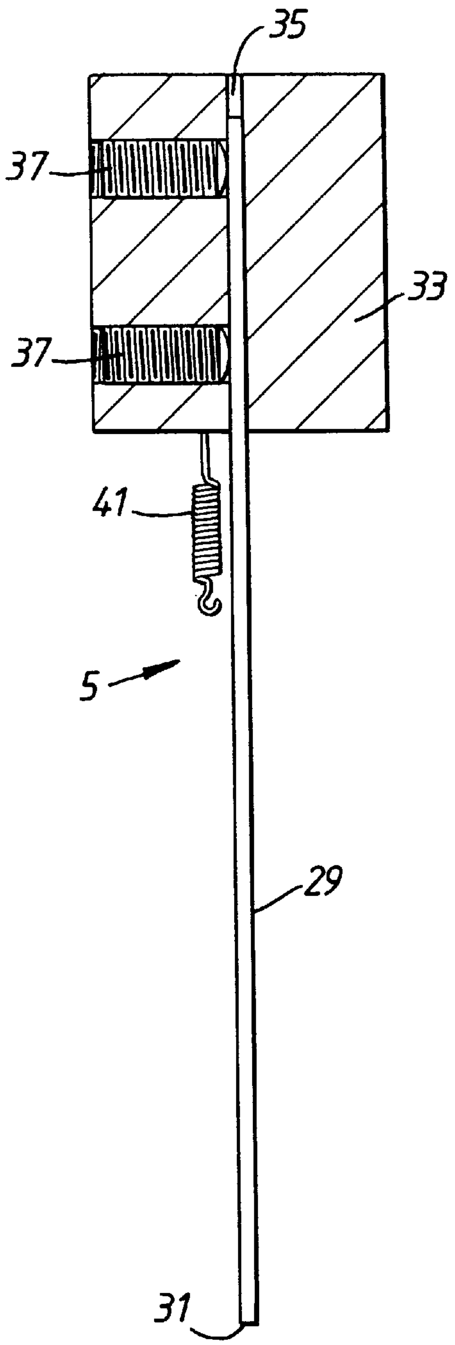
FIG. 10 illustrates the loading component of the insufflator assembly of the second embodiment of the present invention.

In this embodiment, as illustrated in FIG. 9, the sprung component 41 of the loading component 5 comprises a spring and the metering component 3 includes a bent ring 55 instead of the extension 23. By engaging one end of the spring around the bent ring 55 the loading component 5 can be securely retained in relation to the metering component 3 during the step of loading a dose of powder P into the space 39.

It will be appreciated that the flow characteristics of the air flow delivered by the above-described insufflator assemblies will substantially be the same for each delivery, since there is no manual action required to pump air through the insufflator. Furthermore, the air flow provided is instantly both of high pressure and high velocity. Thus, a small volume of air, for instance 1 to 2 ml, is effectively used to deagglomerate the dose of powder P in the space 39 and carry the same into an airway of an animal. This effect is maximized by using a small bore tube for the tubing 53 so as to minimize the dead space downstream of the chamber 45.

In another embodiment the outer dimension of the metering tube 27 of the metering component 3 can be smaller than the inner dimension of the delivery tube 11 of the delivery component 1. A sealing fit of the delivery tube 11 and the metering tube 27 is not essential as the frusto-conical portions 15, 21 of the connectors 13, 19 can be configured to provide a hermetic seal, and thus any air introduced into the metering tube 27 can only pass through the delivery tube 11.

In a further embodiment the metering tube 27 may have generally the same or larger inner and outer dimensions than the delivery tube 11. In this embodiment, however, one or both of the end of the metering tube 27 and the end of the delivery tube 11 which are connected to one another are tapered such that the end of the metering tube 27 is located within the delivery tube 11.

In a still further embodiment one or both of the delivery tube 11 and the metering tube 27 are tapered along either a portion or the entire length.

In each of the above-described embodiments, when the connector 19 of the metering component 3 is fitted to the connector 13 of the delivery component 1, the end of the metering tube 27 is inserted into the delivery tube 11. The frusto-conical portions 15, 21 of the connectors 13, 19 help guide the end of the metering tube 27 into the delivery tube 11, as does, in the second-described embodiment, the inwardly tapering end section of the delivery tube 11.

In a particularly preferred embodiment the inner dimension of the metering tube 27 is no greater than the inner dimension of the delivery tube 11. Thus, when the metering component 3 is fitted to the delivery component 1, a dose of powder P is actually provided within the delivery tube 11 or at least in a direct flow path with the delivery tube 11. It is particularly advantageous for the inner dimension of the delivery tube 11 to be the same or larger than the inner dimension of the metering tube 27, since there is then no obstruction to powder leaving the metering tube 27 and entering the delivery tube 11. This arrangement contrasts with that of known insufflators where the air flow is resisted and constricted in flowing from a relatively large dimension sample chamber into a delivery tube. Furthermore, the known insufflators, in having sample chambers of a size sufficient to allow a user manually to load a dose of powder thereinto, suffer from the drawback that the air flow for carrying the powder is significantly reduced in pressure and velocity. Not only does this reduce the ability of the air flow to pick up the powder from the sample chamber, but also can mean that the smaller dimension delivery tube may provide such a back pressure that the air flow cannot carry the powder, particularly when agglomerated, into the delivery tube. This, in turn, can result in blocking of the opening to the delivery tube.

In a yet further embodiment, in order to provide for adjustment of the length of the elongate member 29 extending from the stop 33, the elongate member 29 can be screwed into the stop 33, possibly with the use of a securing lock nut.

In another alternative embodiment, as a modification of the first-described embodiment, the extension 23 of the connector 19 can be omitted and instead an olive can be fitted to the metering tube 27 to act as the part behind which the sprung component 41 of the loading component 5 engages.

Finally, it will be understood by a person skilled in the art that the present invention has been described in its preferred embodiments and can be modified in many different ways without departing from the scope of the invention as defined in the appended claims. For example, although in the described embodiments elements are used which have a circular cross-section other cross-sections can be used.

What is claimed is:

1. An insufflator assembly, comprising:

an insufflator comprising a delivery component for delivering powder into an airway of an animal, and a metering component containing a predetermined dose of powder for delivery to the delivery component wherein the metering component comprises an inlet for receiving a stream of gas and an outlet connected to said delivery component; and a firing unit for providing a volume of pressurized gas to the inlet so as to carry the dose of powder into the airway of the animal wherein the firing unit comprises a chamber of a predetermined volume for containing gas at a predetermined pressure above atmospheric and the chamber comprises a first valve for selectively connecting the chamber to a pressurized gas source which provides gas and a second valve for selectively connecting the chamber to the inlet of the metering component, whereby both valves can be closed after said chamber has been filled with pressurized gas and said second valve can then be opened to deliver a predetermined volume of air through said metering component and said delivery component to deliver said dose of powder.

2. The insufflator assembly according to claim 1, wherein the predetermined pressure is selectively adjustable.

3. The insufflator assembly according to claim 1 or 2, wherein the predetermined volume of the chamber is selectively adjustable.

4. The insufflator assembly according to claim 1, wherein the chamber comprises an elongate tube.

5. The insufflator assembly according to claim 1, wherein the metering component includes an elongate metering tube having a first open end and a second open end.

6. The insufflator assembly according to claim 5, further comprising a loading component comprising an elongate member having an end face for insertion into a first end of the metering tube and for movement to a predetermined position proximate a second end of the metering tube so as to define a space between the second end of the metering tube and the end face of the elongate member, which space is in use filled with a dose of powder.

7. The insufflator assembly according to claim 6, wherein the loading component further comprises a stop which is fixed to the elongate member and is configured so as to abut the first end of the metering tube when the end face of the elongate member is at the predetermined position.

8. The insufflator assembly according to claim 7, wherein the stop is movable relative to the elongate member so as to provide for adjustment of the distance between the stop and the end face of the elongate member.

9. The insufflator assembly according to claim 8, wherein the stop includes a slot in which the elongate member is slideable and a fixing mechanism for fixing the stop relative to the elongate member.

10. The insufflator assembly according to claim 9, wherein the fixing mechanism comprises at least one screw which in use extends into the stop and selectively abuts a side surface of the elongate member.

11. The insufflator assembly according to claim 7, wherein the loading component further comprises a sprung component having a first end which is engageable with a part of the insufflator so as to retain the stop in abutment with the first end of the metering tube.

12. The insufflator assembly according to claim 11, wherein the metering component includes a part connected to the metering tube and the sprung component of the loading component engages the part when the loading component is fitted to the metering component.

13. The insufflator assembly according to claim 5, wherein the delivery component includes an elongate delivery tube having a first and a second end, the first end for insertion into the airway of the animal and the second end being connectable with the second end of the metering tube.

14. The insufflator assembly according to claim 13, wherein the second end of the delivery tube and the second end of the metering tube are connectable by means of a Luer connection.

15. The insufflator assembly according to claim 14, wherein the second end of the metering tube is configured so as to be insertable into the second end of the delivery tube.

16. A method of providing a stream of gas containing powder, comprising the steps of:

providing an insufflator comprising a metering component loaded with a dose of powder; and providing a stream of gas to an inlet of the insufflator so as to entrain the dose of powder;

characterized in that the step of providing a stream of gas comprises the steps of pressurizing a chamber of a predetermined volume with gas at a predetermined pressure above atmospheric, sealing the chamber and connecting the chamber to the inlet of the insufflator and releasing the pressurized gas from said chamber into the insufflator and entraining the dose of powder in a pressurized volume of gas.

17. The method according to claim 16, wherein the steps of sealing the chamber and connecting the chamber to the inlet of the insufflator include the steps of operating a first valve for selectively connecting the chamber to a pressurized gas source and operating a second valve for selectively connecting the chamber to the inlet of the insufflator.

18. The method according to claim 16, further comprising the step of setting the volume of the chamber to a predetermined volume.

19. The method according to claim 16, further comprising the step of setting the pressure of gas in the chamber to a predetermined pressure.

20. The method according to claim 16, wherein the insufflator includes an elongate metering tube having open ends, and the step of providing an insufflator loaded with a dose of powder comprises the steps of inserting an elongate member having an end face into one end of the metering tube, moving the end face of the elongate member through the metering tube to a predetermined position proximate the other end of the metering tube such as to define a space between the other end of the metering tube and the end face of the elongate member and filing the space in the metering tube with a dose of powder.

21. The method according to claim 20, wherein the loading component further comprises a stop which is fixed to the elongate member, the elongate member being inserted into the metering tube until the stop abuts the one end of the metering tube and the end face of the elongate member is at the predetermined position.

22. The method according to claim 21, further comprising the step of adjusting the distance between the end face of the elongate member and the stop so as to adjust the volume of the space in the metering tube.

* * * * *